US007343001B2

(12) United States Patent
Abu Tabanjeh

(10) Patent No.: US 7,343,001 B2
(45) Date of Patent: Mar. 11, 2008

(54) AUTOMATIC DETECTOR SELECTION BY STUDY TYPE

(75) Inventor: Emad Abu Tabanjeh, Franklin, WI (US)

(73) Assignee: General Electric Company, Schenectady, NY (US)

( * ) Notice: Subject to any disclaimer, the term of this patent is extended or adjusted under 35 U.S.C. 154(b) by 211 days.

(21) Appl. No.: 11/306,882

(22) Filed: Jan. 13, 2006

(65) Prior Publication Data

US 2007/0165783 A1 Jul. 19, 2007

(51) Int. Cl.
*H05G 1/58* (2006.01)

(52) U.S. Cl. ...................................... 378/116; 378/115

(58) Field of Classification Search ................ 378/115, 378/116
See application file for complete search history.

(56) References Cited

U.S. PATENT DOCUMENTS 6,859,521 B2 * 2/2005 Spahn ........................ 378/116
6,950,496 B2 * 9/2005 Zimmermann et al. ..... 378/116
7,250,608 B2 * 7/2007 Ozeki .................... 250/370.09

* cited by examiner

*Primary Examiner*—Chih-Cheng G Kao

(57) ABSTRACT

Methods of using an X-ray system having a central computer system, an X-ray source and a bank of wireless detectors. The methods include an automated X-ray system that requires the input of a type of X-ray to be performed on a patient, and the systems determine and identify which detector from the detector bank is appropriate for the ordered test.

20 Claims, 4 Drawing Sheets

AUTOMATIC DETECTOR SELECTION BY STUDY TYPE

TECHNICAL FIELD

The present invention relates generally to X-ray systems and more particularly to an X-ray system including wireless detectors of various sizes.

BACKGROUND OF THE INVENTION

X-ray systems are commonly used in the medical field to assist medical professionals in diagnosing ailments in patients. It is known that the hardware required for taking an X-ray includes an X-ray source and a detector. Although the need for these two fundamental components remains constant, throughout the years the components have evolved.

Originally it was known to use one standard size detector for any given X-ray system and the detector utilized film to capture the image. One disadvantage of this system resulted in the patient potentially being exposed to more radiation than necessary during any given X-ray since the size of the detector could not be changed. Yet another disadvantage of this type of system is that the film needed to be processed to be useful which resulted in a time consuming endeavor.

Now, it is known to use digital X-ray detectors. The digital detector is hard-wired to a computer system where the results are digitally fed into a computer system and read on a monitor. This results in a faster final product, but the size of the detector remains constant.

The newest X-ray technology includes wireless digital detectors. These systems are capable of utilizing various sized wireless detectors that can be used with a single X-ray source. This technology is still in its infancy, so users are struggling with how to efficiently use this type of system both from a hardware perspective and an information processing perspective. While it is advantageous to have flexibility in the size detector used for any given X-ray, a disadvantage of this type of wireless system is that it is time consuming for the X-ray technician to evaluate the type of X-ray being taken, determine which detector is the optimal size to use, and which detector is charged and available for use. Additionally, it is time consuming to identify studies that are being performed for particular types of X-ray data obtained and associate the obtained data with the identified studies.

SUMMARY OF THE INVENTION

It is therefore an object of the present invention to provide an automated X-ray system including various sized wireless digital detectors. The hardware required includes a computer system and a bank of various sized detectors that are in wireless communication with the computer system. The present invention provides a more efficient X-ray system than known systems. It is more efficient by providing a system that requires less time to determine which detector to use for an ordered X-ray, automatically transmitting the results to the computer system, and automatically pairing the results of the X-ray with any ongoing studies analyzing the captured data.

The proposed invention includes inputting a patient identification parameter into the computer system along with the type of X-ray to be performed on the identified patient. The computer system determines which detector to use from the bank of detectors and then transmits an activation signal to the selected detector. After receiving the activation signal the selected detector will activate an indicator to notify an operator of the system that it is the selected detector. The selected detector includes a display screen in which the patient identification will be displayed. The selected detector is placed in position and captures the data for the ordered X-ray image. Once the data is captured it is wirelessly transmitted to the computer system. The computer system will then identify any ongoing studies that are utilizing or analyzing data from the ordered X-ray and associate the data from the X-ray with the identified ongoing studies.

Other features of the present invention will become apparent when viewed in light of the detailed description and preferred embodiment when taken in conjunction with the attached drawings and claims.

DESCRIPTION OF PREFERRED EMBODIMENTS

Figure 1:
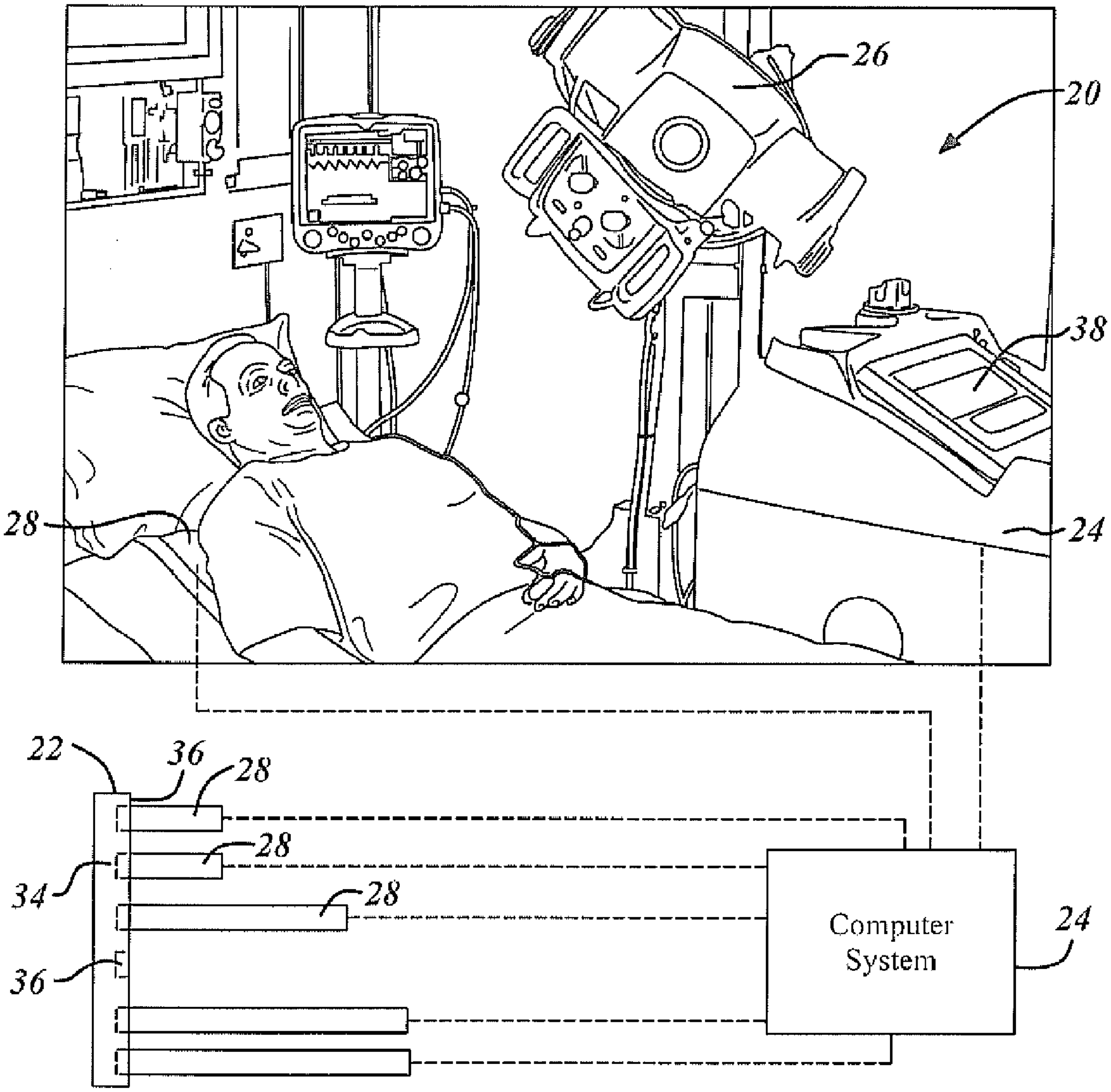
FIG. 1 is a perspective view of the hardware used for an X-ray system in accordance with an embodiment of the present invention.

In the following figures the same reference numerals will be used to refer to the same components and methods. In the following description, various operating parameters and components are described for one constructed embodiment. These specific parameters and components are included as examples and are not meant to be limiting.

Also, in the following description various X-ray components, assemblies, and methods are described as an illustrative example. The X-ray components, assemblies, and methods may be modified depending upon the application.

Referring now to FIG. 1, a perspective view of a X-ray system 20 utilizing a bank of wireless detectors 22 in accordance with an embodiment of the present invention is shown. The X-ray system 20 includes a computer system 24, an X-ray source 26, and a bank of various sized wireless detectors 22. Each wireless detector 28 is capable of transmitting and receiving data to and from the computer system 24 without being hard wired into the system and, similarly, the computer system 24 is capable of transmitting and receiving wireless data.

Figure 2:
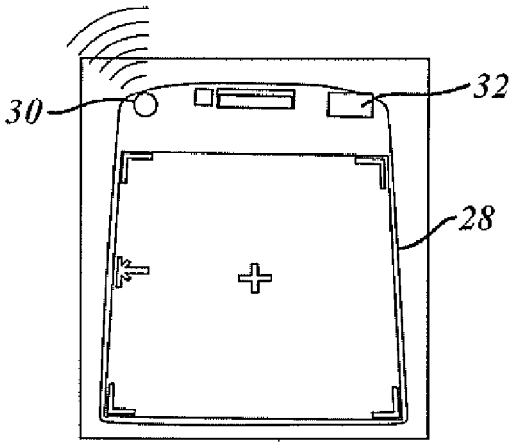
FIG. 2 is front view of a detector used with an X-ray system in accordance with an embodiment of the present invention.

Further, each wireless detector 28 in the bank 22 may include an indicator 30 and/or a display screen 32 as illustrated in FIG. 2. The indicator 30 may be a visual signal, including, but not limited to a light from a light emitting diode ("LED") or a standard bulb. The light may either stay on or flash. Another possible option for the indicator includes an audio signal that sounds when the detector has been selected. The audio signal could include, but is not limited to, a beep or a siren. The indicator 30 could also be a combination visual signal and audio signal.

Figure 3:
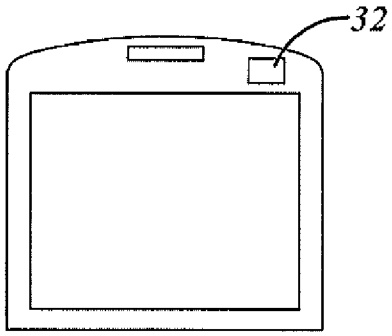
FIG. 3 is a front view of an alternative detector used with an X-ray system in accordance with an embodiment of the present invention.

In accordance with an embodiment of the present invention the display screen 32 located on the detector 28 can display a variety of information. The information displayed, also referred to as instructional information, could include, but is not limited to, a patient identification parameter and any on-going studies that utilize the data captured by the particular X-ray that has been ordered. Of course, a user or operator of the system can determine which data to display on the screen. In one embodiment, as illustrated in FIG. 3, the display screen 32 acts as the indicator by displaying the patient identification. In this embodiment there is no other indicator, only the display screen displaying the patient identification parameter.

A scenario in accordance with the teachings of the present invention involves a doctor or medical professional ordering an X-ray to be performed on a patient for diagnostic purposes. It is recognized that this scenario is often performed in a hospital setting. However, it is also recognized that X-ray systems and methods can be used in any number of environments where X-ray data is obtained from subjects, including but not limited to hospitals, clinics, veterinarian hospitals or veterinarian clinics.

Figure 4:
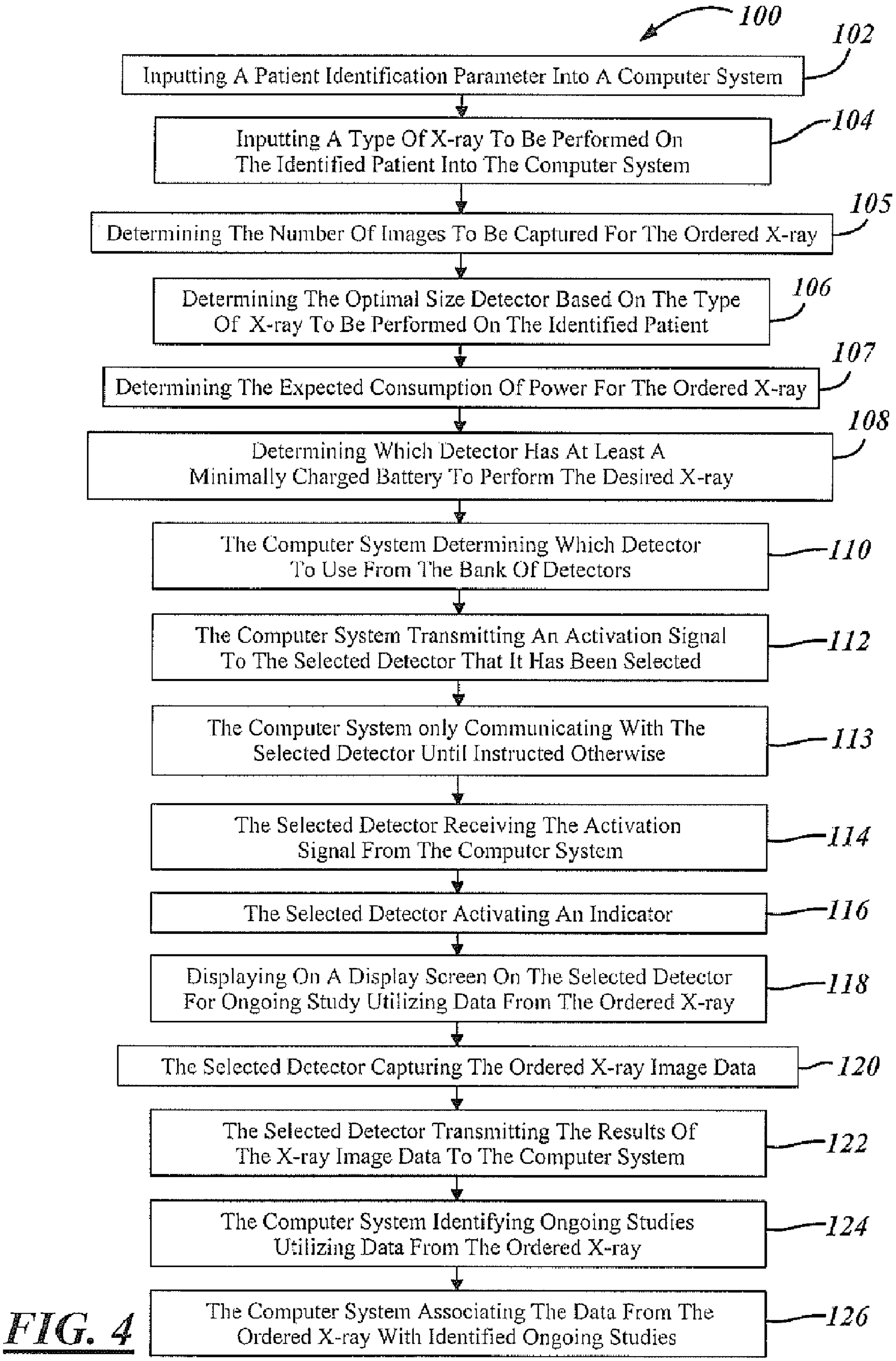
FIGS. 4-6 are flowcharts of methods in accordance with embodiments of the present invention.
Figure 5:
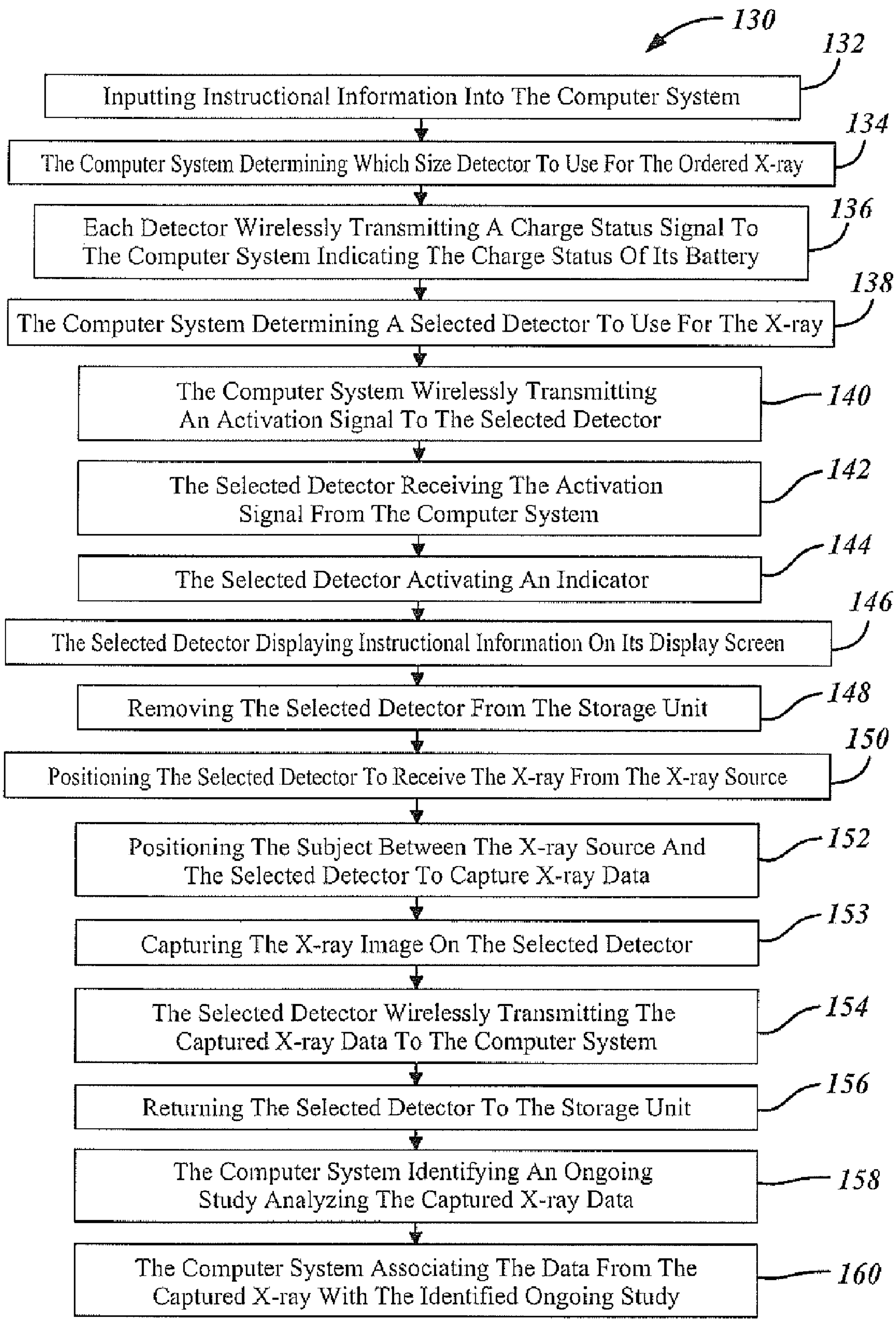
Figure 6:
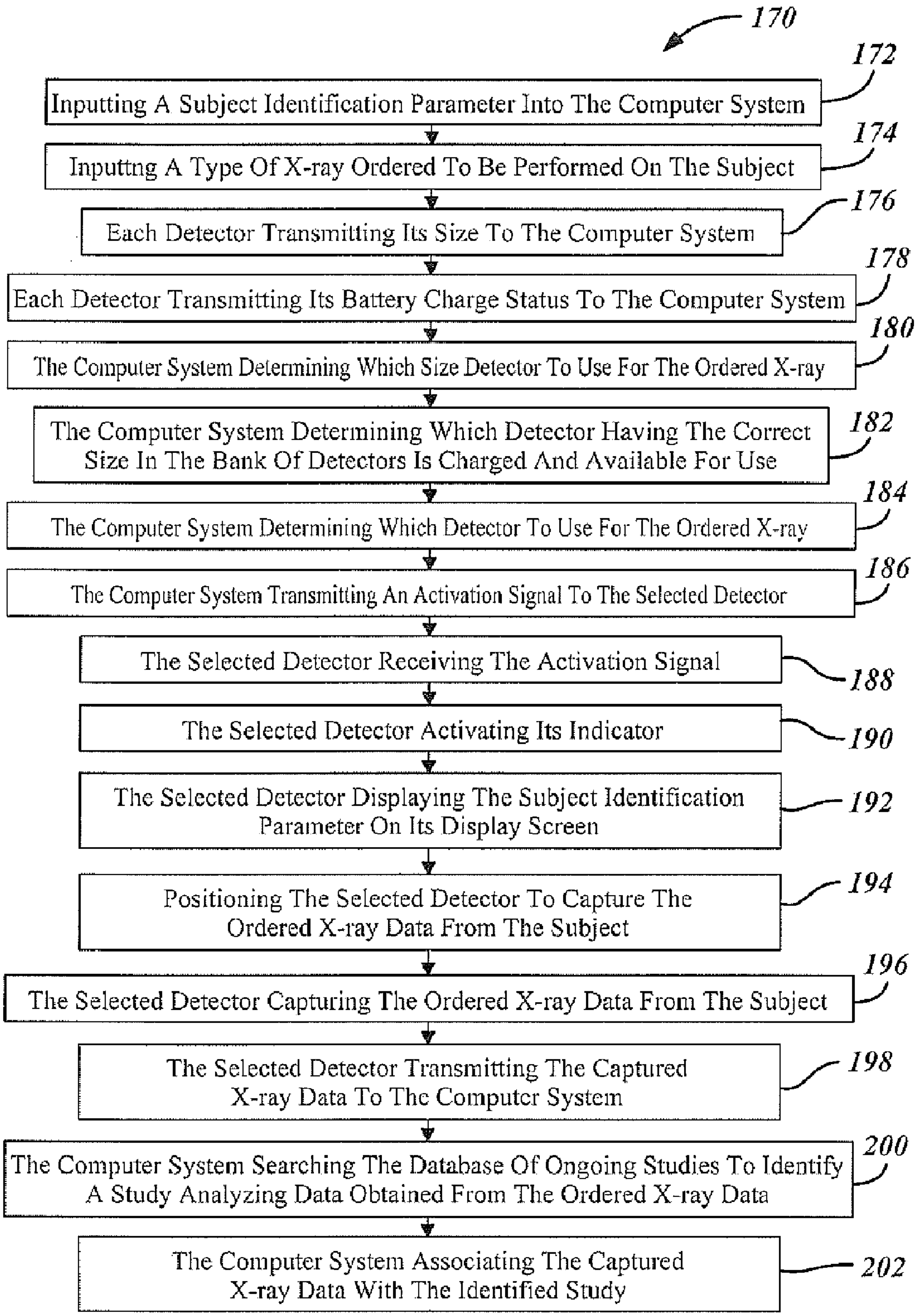

FIGS. 4-6 illustrate the flowcharts 100, 130, 170 outlining the steps for various embodiments in accordance with the teachings of the present invention. There are two data parameters entered into the computer system 102, 104, 132, 172, 174. The data parameters are also referred to as instructional information. The first parameter is a patient or subject identification parameter. The patient identification parameter could be the patient's name or an identification number. The second parameter is the type of X-ray ordered by the medical professional to be performed on the patient or subject. Another factor is determining the number of images to be captured for the ordered X-ray 105. The computer system processes this information and determines which detector from the bank should be used for the ordered X-ray 110, 138, 182, 184. The computer system will also determine any on-going studies utilizing the data from the ordered X-ray 124, 158, 200.

A detector is selected based on several different factors. One factor considers the size of the detector with respect to the type of X-ray to be performed 106, 134, 180. An optimal detector is big enough to capture the entire area of interest, yet small enough to limit the amount of radiation exposure by the patient. Another factor is determining the expected consumption of power for the ordered X-ray 107. Another factor considers whether the detector is charged and available for use 108, 182.

Since the detectors are wireless they contain batteries that need to be charged. In one embodiment in accordance with the present invention the bank of detectors 22 is stored in a storage unit 34 where they are stationed when not in use. The storage unit 34 contains slots 36 into which a detector 28 is positioned and connected to recharge its battery. The detectors 28 are positioned within the unit 34 so that any visual indicator is visible and any audio indicator is audible to an operator of the system without removing the detector 28 from the storage unit 34.

Each detector 28 transmits information to the computer system 24. The information transmitted includes its size and its charge status 136, 176, 178. The charge status signal indicates whether the detector's battery is fully charged or not. If the detector's battery is fully charged it is available for use.

Therefore, the computer system 24 will determine the selected detector based on the optimal size detector and which of the detectors having the desired size are charged and available in the bank. Once the specific detector has been determined the computer system will transmit an activation signal to the selected detector notifying the specific detector that it has been selected 112, 140, 186. The computer system is only communicating with the selected detector until instructed otherwise 113.

When the selected detector receives the activation signal 114, 142, 188 its indicator will be activated 116, 144, 190. As previously discussed the indicator 30 could either illuminating a light, emitting an audio signal, a combination of the two or some other type of indicator to distinguish it from the other detectors in the bank. Additionally, the display screen 32 on the detector 28 may show the patient's or subject's identification parameter and any ongoing studies associated with the particular X-ray ordered 118, 146, 192.

The X-ray technician or operator will receive a notice of the order for a particular patient or subject via the computer system 24 and also from the selected detector's indicator 30. The operator will remove the selected detector from the storage unit 148 and load the selected detector into the proper position for obtaining the ordered X-ray 150, 194. The patient or subject will then be positioned between the X-ray source and the selected detector so that the selected detector can capture the ordered X-ray data 152.

The ordered X-ray is taken when the X-ray from the source passes through the subject and the resultant image is captured on the selected detector 120, 153, 196. The results are digitally captured by the selected detector and wirelessly transmitted back to the computer system to be analyzed by a doctor or medical professional 122, 154, 198. In one embodiment in accordance with the teachings of the present invention the data can be analyzed on a computer monitor 38 that is part of the computer system 24. When the X-ray is complete the operator will remove the selected detector 28 and position it back in the storage unit 34 to be recharged 156.

The computer system identifies any ongoing studies utilizing or analyzing the data from the ordered X-ray by searching a database of on-going studies 124, 158, 200. Further, the computer system associates or matches the type of X-ray ordered or captured data with any identified ongoing studies 126, 160, 202.

This provides a more efficient system in terms of patient logistics and time consumption compared to known systems. The operator can prepare the equipment prior to the patient or subject's arrival. Further, there is minimal effort required by the operator since the selected detector will be obvious due to it's activated indicator 30.

While the invention has been described in connection with one or more embodiments, it is to be understood that the specific mechanisms and techniques which have been described are merely illustrative of the principles of the invention, numerous modifications may be made to the methods and apparatus described without departing from the spirit and scope of the invention as defined by the appended claims.

What is claimed is:

1. A method of selecting a wireless detector in an X-ray system wherein the X-ray system includes a computer system and a bank of various sized detectors in wireless communication with the computer system, the method comprising the steps of:

inputting a patient identification parameter into a computer system;

inputting a type of X-ray to be performed on the identified patient into the computer system;

the computer system determining which detector to use from the bank of detectors;

the computer system transmitting an activation signal to the selected detector that has been selected;

the selected detector receiving the activation signal from the computer system;

the selected detector activating an indicator;

the selected detector capturing the ordered X-ray image data;

the selected detector transmitting the results of the X-ray image data to the computer system;

the computer system identifying ongoing studies utilizing data from the ordered X-ray; and the computer system associating the data from the ordered X-ray with identified ongoing studies.

2. The method of selecting a wireless detector in an X-ray system of claim 1 wherein determining which detector to use from the bank further comprises the steps of:

determining the optimal size detector based on the type of X-ray to be performed on the identified patient; and determining which detector has a charged battery and is available for use.

3. The method of selecting a wireless detector in an X-ray system of claim 1 wherein activating an indicator includes illuminating a light on the selected detector.

4. The method of selecting a wireless detector in an X-ray system of claim 1 wherein activating an indicator includes emitting an audio signal from the selected detector.

5. The method of selecting a wireless detector in an X-ray system of claim 1 wherein activating an indicator includes illuminating a light on the selected detector and emitting an audio signal from the selected detector.

6. The method of selecting a wireless detector in an X-ray system of claim 1 wherein activating an indicator includes displaying on a display screen on the selected detector the patient's identification parameter.

7. The method of selecting a wireless detector in an X-ray system of claim 1 further comprising the step of displaying on a display screen on the selected detector an ongoing study utilizing data from the ordered X-ray.

8. The method of selecting a wireless detector in an X-ray system of claim 1 wherein the computer system identifies ongoing studies by searching a database of ongoing studies and matches the type of X-ray ordered with specific studies analyzing data for the type of X-ray ordered.

9. A method of taking an X-ray of a subject, wherein the X-ray system includes a computer system capable of transmitting and receiving wireless data, an X-ray source, a bank of various sized detectors wherein each detector includes an indicator, a display screen, and each detector is in wireless communication with the computer system, and a storage unit for storing and charging batteries of the detectors, the method comprising the steps of:

inputting instructional information into the computer system;

the computer system determining which size detector to use for an ordered X-ray;

each detector wirelessly transmitting a charge status signal to the computer system indicating the charge status of its battery;

the computer system determining a selected detector to use for the X-ray;

the computer system wirelessly transmitting an activation signal to the selected detector;

the selected detector receiving the activation signal from the computer system;

the selected detector activating an indicator;

removing the selected detector from the storage unit;

positioning the selected detector to receive the X-ray from the X-ray source;

positioning the subject between the X-ray source and the selected detector to capture X-ray data;

capturing an X-ray image on the selected detector; and the selected detector wirelessly transmitting the captured X-ray data to the computer system.

10. The method of claim 9 further comprising the step of returning the selected detector to the storage unit.

11. The method of claim 9 further comprising the steps of:

the computer system identifying an ongoing study analyzing the captured X-ray data; and the computer system associating the data from the captured X-ray with the identified ongoing study.

12. The method of claim 9 further comprising the step of the selected detector displaying instructional information on its display screen.

13. The method of claim 9 wherein the instructional information includes a subject identification parameter and the type of X-ray ordered.

14. The method of claim 9 wherein the charge status signal is battery fully charged or battery not fully charged.

15. The method of claim 9 wherein activating the indicator includes illuminating a light on the selected detector.

16. The method of claim 9 wherein activating the indicator includes emitting an audio signal from the selected detector.

17. A method of selecting a detector in an X-ray system for obtaining X-ray data of a subject wherein the X-ray system includes a computer system capable of transmitting and receiving data wirelessly and including a database of ongoing studies, an X-ray source, and a bank of various sized detectors each capable of transmitting and receiving data wirelessly and each including an indicator and a display screen, the method comprising the steps of:

inputting a subject identification parameter into the computer system;

inputting a type of X-ray ordered to be performed on the subject;

the computer system determining which detector to use for the ordered X-ray;

the computer system transmitting an activation signal to the selected detector;

the selected detector receiving the activation signal;

the selected detector activating its indicator;

the selected detector displaying the subject identification parameter on its display screen;

positioning the selected detector to capture the ordered X-ray data from the subject;

the selected detector capturing the ordered X-ray data from the subject;

the selected detector transmitting the captured X-ray data to the computer system;

the computer system searching the database of ongoing studies to identify a study analyzing data obtained from the ordered X-ray data.

18. The method of claim 17 further comprising the step of the computer system associating the captured X-ray data with the identified study.

19. The method of claim 17 wherein the computer system determining which detector to use for the ordered X-ray comprises the steps of:

each detector transmitting its size to the computer system;

each detector transmitting its battery charge status to the computer systems;

the computer system determining which size detector to use for the ordered X-ray; and the computer system determining which detector having the correct size in the bank of detectors is charged and available for use.

20. The method of claim 17 wherein activating an indicator includes illuminating a light on the selected detector.

* * * * *